United States Patent [19]
Weber et al.

[11] Patent Number: 5,741,891
[45] Date of Patent: Apr. 21, 1998

[54] PULMONARY SURFACTANT PEPTIDE SOLUBILIZATION PROCESS

[75] Inventors: James V. Weber, Newton, Pa.; Charles F. Kasulanis, High Bridge; Keith Sampino, Parsippany, both of N.J.

[73] Assignee: Ortho Pharmaceutical Corporation, Raritan, N.J.

[21] Appl. No.: 735,171

[22] Filed: Oct. 22, 1996

Related U.S. Application Data

[60] Provisional application No. 60/007,347 Nov. 20, 1995.
[51] Int. Cl.$^6$ ............................ A61K 38/00; C07K 5/00; C07K 7/00
[52] U.S. Cl. ..................... 530/326; 530/345; 530/333; 514/13
[58] Field of Search .................. 514/11, 12, 13, 514/14, 15; 530/320, 325, 326, 327, 328, 324, 333, 344, 345

[56] References Cited

U.S. PATENT DOCUMENTS

| | | | |
|---|---|---|---|
| 4,861,756 | 8/1989 | Jackson | 514/11 |
| 5,164,369 | 11/1992 | Cochrane et al. | 514/12 |

FOREIGN PATENT DOCUMENTS

| | | |
|---|---|---|
| WO 9222315 | 12/1992 | European Pat. Off. . |
| WO 9308824 | 5/1993 | European Pat. Off. . |
| 9222315 | 12/1992 | WIPO .............. A61K 37/02 |

OTHER PUBLICATIONS

International Search Report—International Application No. PCT/US96/16804—International Filing Date 22. Oct. 1996.

Database Medline, Abstract 93360135. XP2024935, Journal of Pharmacology and Experimental Therapeutics, (1993 Aug.) 266 (2) 551–6.

Database Medline, Abstract 93312859, XP2024934, Biochimica et Biophysica Acta, (1993 Jul. 1) 1168 (3) 261–70.

*Primary Examiner*—Avis M. Davenport
*Attorney, Agent, or Firm*—Kenneth J. Dow

[57] ABSTRACT

The invention relates to a method of manufacturing pulmonary surfactant protein by solubilizing the protein in ethanol by treatment with a fluorinated alcohol so that the protein may be formulated into liposomes by ethanolic injection.

7 Claims, 10 Drawing Sheets

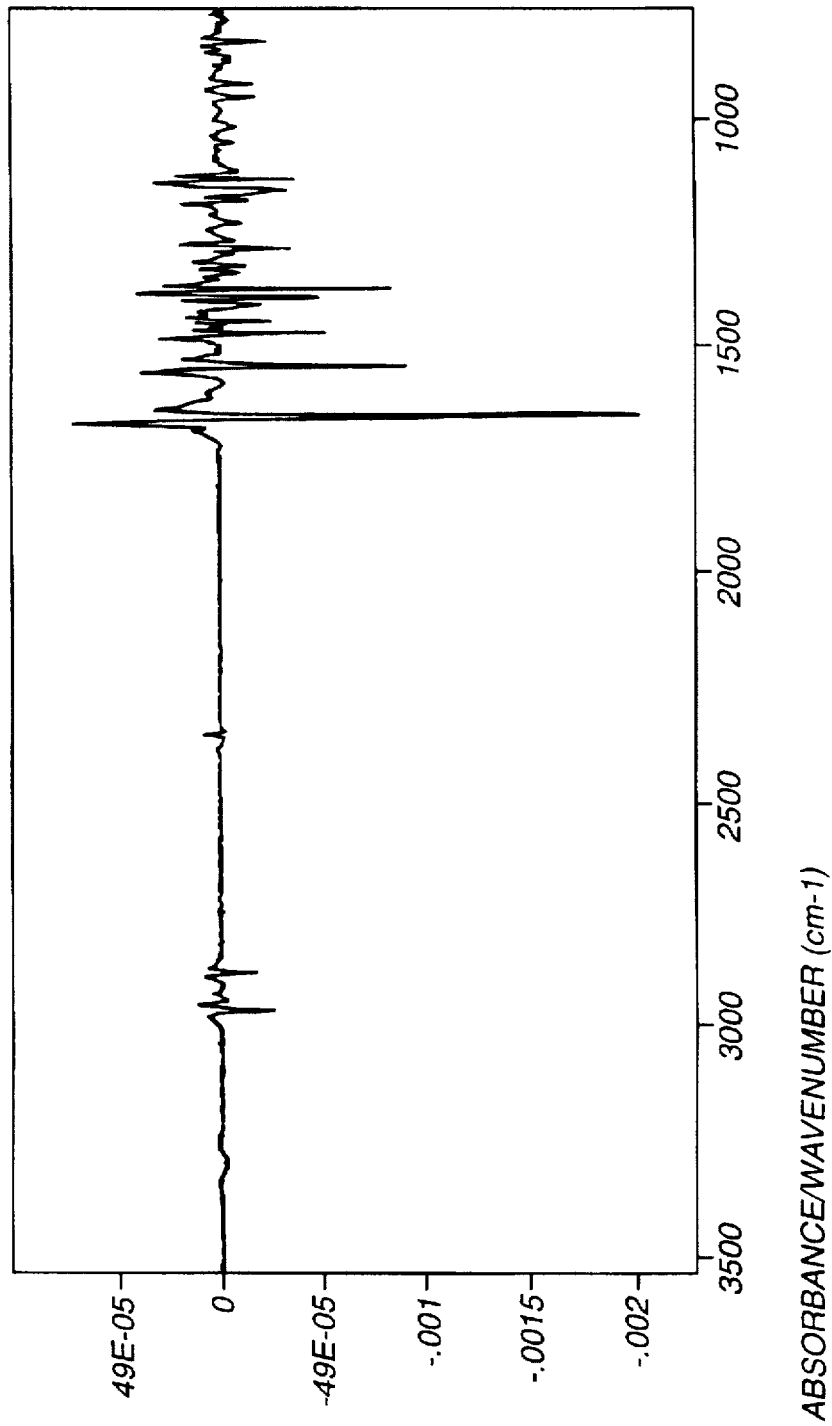

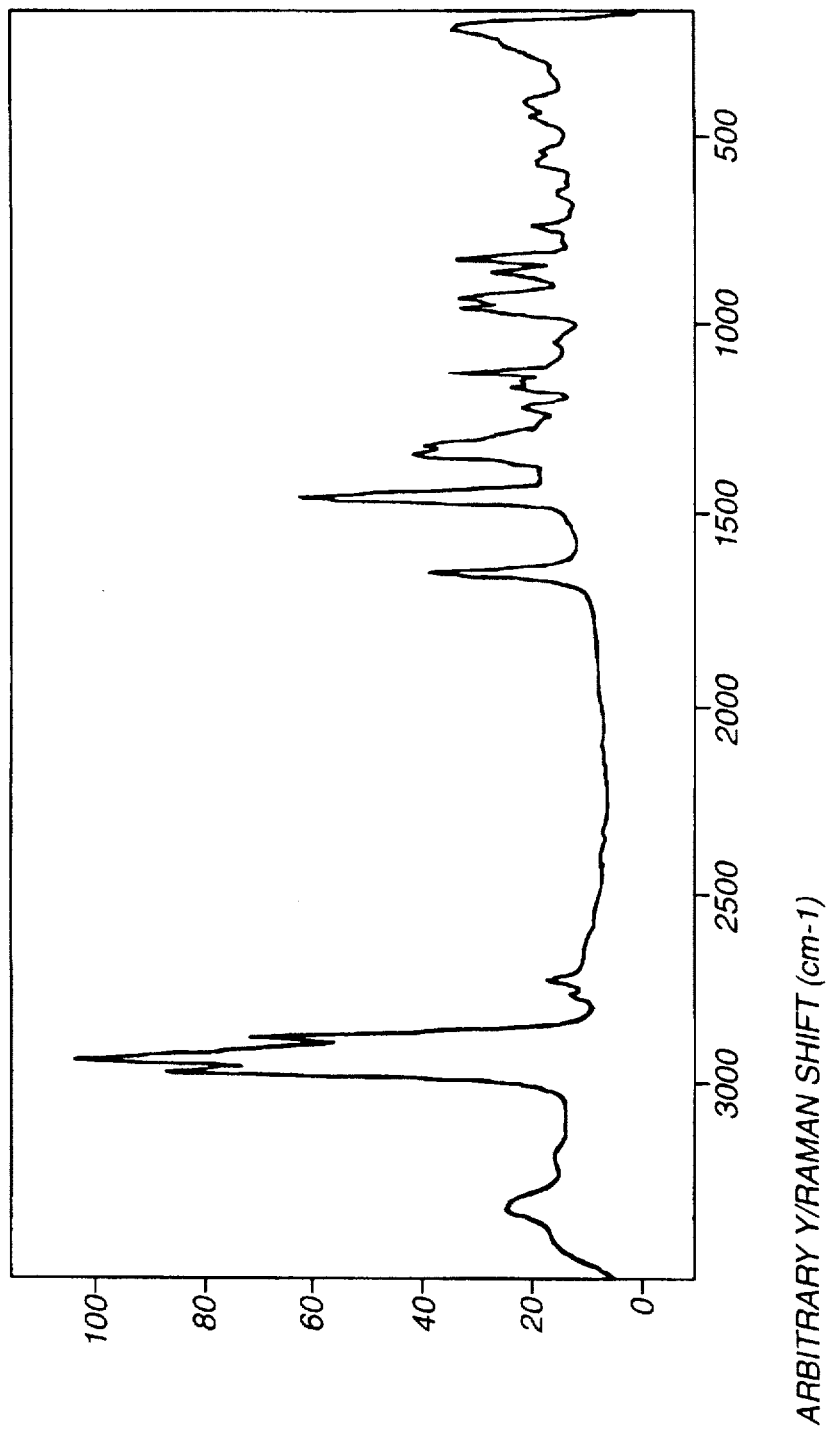

PULMONARY SURFACTANT PEPTIDE SOLUBILIZATION PROCESS

This application claims the benefit of U.S. Provisional application Ser. No. 60/007,347, filed Nov. 20, 1995.

FIELD OF THE INVENTION

The present invention relates to the field of pharmaceutical compositions and the manufacture of liposomal pulmonary surfactant protein compositions by ethanolic injection. More particularly, the invention relates to a method of solubilizing pulmonary surfactant protein in ethanol by treatment with a fluorinated alcohol so that the protein may be formulated into liposomes by ethanolic injection.

BACKGROUND OF THE INVENTION

Pulmonary surfactant is a complex mixture of lipids and proteins that promotes the formation of a monolayer at the alveolar air-water interface and, by reducing the surface tension, prevents the collapse of the alveolus during expiration. Premature infants, and occasionally full term neonates, sometimes suffer from a condition known as respiratory distress syndrome (RDS) due to the lack of sufficient endogenous pulmonary surfactant. Artificial pulmonary surfactants have therefore been developed to treat this condition thereby reducing infant morbidity and mortality. Likewise, artificial pulmonary surfactants have also been indicated in the treatment of adult respiratory distress syndrome.

One of these artificial pulmonary surfactants, known as $KL_4$, is disclosed in U.S. Pat. Nos. 5,164,369 and 5,260,273. As described therein, $KL_4$ is a synthetic pulmonary surfactant composition comprising a pharmaceutically acceptable phospholipid admixed with a polypeptide having alternating hydrophobic and positively charged amino acid residues. As formulated for clinical use, the composition is a liposome comprised of dipalmitoyl-phosphatidylcholine (DPPC), palmitoyloleoylphophatidylglycerol (POPG), palmitic acid (PA) and the synthetic peptide $KL_4$ suspended in a buffered aqueous medium. The final drug product is a liposomal suspension intended for direct instillation into the lung.

As mentioned, the artificial pulmonary surfactant, $KL_4$, is a liposomal formulation. Liposomes are small vesicles comprising amphipathic lipids arranged in spherical bilayers. Liposomes may contain many concentric lipid bilayers separated by aqueous channels (multilamellar vesicles or MLVs), or alternatively, they may contain a single membrane bilayer (unilamellar vesicles), which may be small unilamellar vesicles (SUVs) or large unilamellar vesicles (LUVs). The lipid bilayer is composed of two lipid monolayers having a hydrophobic "tail" region and a hydrophilic "head" region. In the membrane bilayer, the hydrophobic "tails" of the lipid monolayers orient towards the center of the bilayer, whereas the hydrophilic "heads" orient toward the aqueous phase.

Liposomes may be used to encapsulate a variety of materials by trapping hydrophilic compounds in the aqueous interior or between bilayers, or by trapping hydrophobic compounds within the bilayer. As such, they are particularly useful to deliver biologically active materials by encapsulating compounds which exhibit poor aqueous solubility or which exhibit unacceptable toxicity at therapeutic dosages.

Liposomes and related phospholipid vesicle complexes can be prepared by a variety of techniques. In general, these techniques start with "dry" lipids that are introduced into an aqueous phase (D. Lasic, J. Theor. Biol. (1987) 124: 35–41). Once the lipid is hydrated, liposomes form spontaneously. Techniques have been developed to control the number of lamellae in the liposome and to produce defined particle size.

One method of preparing liposomes is known as the ethanolic injection process as described in (S. Batzre et al., *Biochem. Biophys Acta* (1973) 298: 1015–1019; J. Kremer at al., *Biochemistry* (1977) 16: 3932–3935) hereby incorporated by reference into the present application. In this process, the lipids and active ingredient are dissolved in ethanol and injected into the aqueous phase, optionally containing a buffer solution. This process generates unilamellar vesicles of defined size and is particularly well suited for manufacture of $Kl_4$ pulmonary surfactant.

Accordingly, at present, this liposomal $KL_4$ composition is formulated by the aforementioned ethanolic injection process. The formulation process requires the $KL_4$ peptide ingredient to be dissolved in 95% ethanol for manufacture into liposomes. However, $KL_4$ peptide, prepared by solid phase synthesis, exhibits extremely poor solubility in ethanol of approximately 1 mg/ml in 95% ethanol. One method that has been used on a small scale to enhance the solubility of the peptide involves lyophilization of the peptide at a low concentration in a mixed aqueous/organic solvent system. However, this process is not particularly suitable for use on a large scale when cost and through-put of material are considered.

Accordingly, there is a need for an improved process for solubilizing $KL_4$ peptide in ethanol for manufacture into liposomes.

SUMMARY OF THE INVENTION

The invention involves an improvement in the process of preparing liposomal pulmonary surfactant composition by ethanolic injection, wherein the composition is comprised of a polypeptide and a pharmaceutically acceptable phospholipid. The improvement comprises preparing a form of the polypeptide, or salt or ester thereof, which exhibits enhanced solubility in ethanol, comprising the steps of:

(a) preparing a solution of the polypeptide or salt or ester thereof in a fluorinated alcohol at a concentration of about 5 to 40 mg/ml;

(b) incubating for a period of time sufficient to achieve an optical density at 450 nanometers of less than 0.06;

(c) filtering; and (d) removing the fluorinated alcohol to recover solid, soluble polypeptide.

The polypeptide useful in the present invention is disclosed in U.S. Pat. Nos. 5,164,369 and 5,260,273. It is a linear polypeptide comprising at least 10 amino acid residues and no more than 60 amino acid residues, including a sequence having alternating hydrophobic and hydrophilic amino acid regions represented by the formula $(Z_aU_b)_cZ$ wherein:

Z is a hydrophilic amino acid residue independently selected from the group consisting of R and K;

U is a hydrophobic amino acid residue independently selected from the group consisting of V,I,L, C and F;

a has an average value of about 1 to about 5;

b has an average value of about 3 to about 20;

c is 1 to 10; and d is 1 to 3.

Particularly preferred is the polypeptide $KL_4$ which has a amino acid sequence KLLLLKLLLLKLLLLKLLLLK.

It is known that these synthetic polypeptides, including $KL_4$, can adopt a variety of secondary structures including α-helical, β-pleated, β-sheet or random coil secondary structure. The α-helical form appears to exhibit the greatest solubility in ethanol. Accordingly, it is postulated that the process of the present invention enhances the solubility of the polypeptide by inducing an α-helical secondary structure in the polypeptide. The polypeptide prepared by treatment with fluorinated alcohol in accordance with the present invention exhibits enhanced solubility in 95% ethanol and is thus made suitable for use in the ethanol injection process of preparing liposomal pulmonary surfactant compositions.

In another aspect of the invention, the polypeptide can be solubilized in the fluorinated alcohol and the resulting solution can be admixed with the ethanol solvent for use directly in the ethanol injection process. The fluorinated alcohol can then be removed along with the ethanol solvent by dialysis or evaporation in the liposome manufacturing process. Trifluoroethanol ("TFE") is the preferred fluorinated alcohol.

BRIEF DESCRIPTION OF THE DRAWINGS

FIGS. 3A and 3B show the FT-IR spectra of the solid polypeptide, $KL_4$-Acetate, treated in accordance with the present invention.

FIGS. 4A and 4B show the FT-RAMAN spectra of the solid polypeptide, $KL_4$-Acetate, treated in accordance with the present invention.

DETAILED DESCRIPTION

Figure 1:
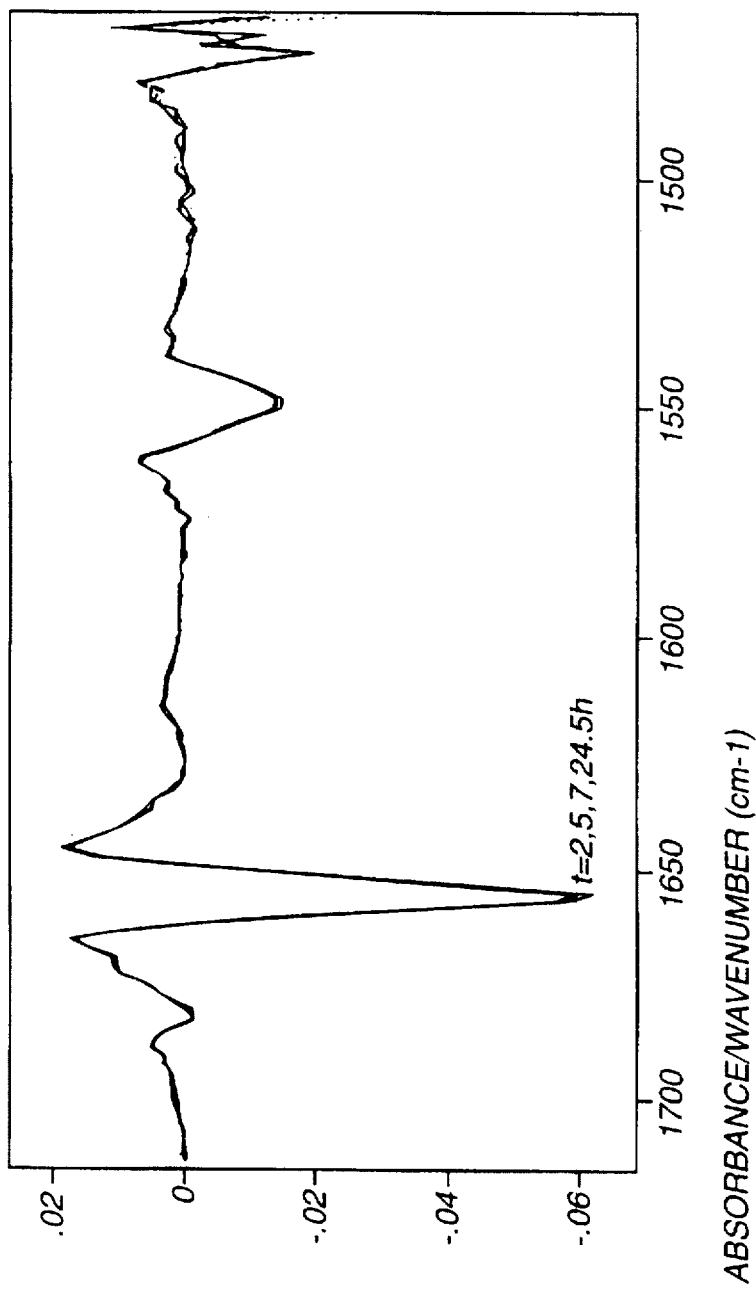
FIG. 1 shows the FT-IR spectra of the polypeptide, $KL_4$-Acetate, in TFE during the incubation, treated in accordance with the present invention.

All amino acid residues identified herein are in the natural L-configuration. Consistent with standard polypeptide nomenclature, *J. Biol. Chem.* 243: 3557–59 (1969), abbreviations for amino acid residues are as shown in the following Table of Correspondence:

| Table of Correspondence | | |
|---|---|---|
| Symbol | | |
| 1-Letter | 3-Letter | Amino Acid |
| Y | Tyr | L-Tyrosine |
| G | Gly | Glycine |
| F | Phe | L-Phenylalanine |
| M | Met | L-Methionine |
| A | Ala | L-Alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |

-continued

| Table of Correspondence | | |
|---|---|---|
| Symbol | | |
| 1-Letter | 3-Letter | Amino Acid |
| Q | Gln | L-glutamine |
| E | Glu | L-glutamic acid |
| W | Trp | l-tryptophan |
| R | Arg | l-arginine |
| D | Asp | l-aspartic acid |
| N | Asn | L-asparagine |
| C | Cys | l-cysteine |

The amino acid residues represented herein by formulae are in the left to right orientation in the conventional direction of amino-terminus to carboxyl-terminus.

The artificial pulmonary surfactant polypeptides for use in the invention may be prepared by any techniques that are well known to those skilled in the art, for example by solid phase synthesis, by recombinant DNA techniques, or by classical solution synthesis. Methods for the production of the polypeptides are described in U.S. Pat. No. 5,164,369, hereby incorporated by reference into the present application.

When prepared by these various techniques, particularly when solid phase synthesis of the polypeptide is employed, the resulting polypeptide can exhibit variable secondary structure and variable solubility in ethanol. When solid phase synthesis is employed, the main secondary structure appears to be anti-parallel β-sheet which exhibits poor solubility in ethanol. However, when the polypeptide is treated with a fluorinated alcohol in accordance with the present invention, the predominant secondary structure exhibited by the polypeptide is α-helical and the solubility of the polypeptide in ethanol is improved. Moreover, treatment of the polypeptide with the fluorinated alcohol minimizes aggregation of the polypeptide in solution and improves processing.

The process is carried out by adding the pulmonary surfactant polypeptide to a solution of the fluorinated alcohol at a concentration of 5–40 mg/ml. The resulting suspension is then incubated with stirring for sufficient time to dissolve the polypeptide. Incubation time may vary from batch to batch. Sufficient incubation time should be employed to allow de-aggregation of the polypeptide yielding a clear, non-viscous solution. Adequate de-aggregation is reached when the solution exhibits an optical density measurement of light scattering at 450 nanometers of less than 0.06, preferably 0.03 or less.

The aggregation is monitored by measuring the apparent absorbance at 450 nm (OD450) which result from light scattering of the aggregates within the sample. A UV/Vis spectrophotometer with the wavelength set to 450 nm is used for the measurements. Sample compartment configuration of the instrument must be such to allow the accurate measurement of light scattering. Instruments which have been tested and which meet the requirements are the Perkin Elmer LAMBDA 14 UV/Vis spectrometer and the Shimadzu DU260 UV/Vis spectrometer.

Generally the $KL_4$ peptide is incubated in TFE for 2 to 24 hours followed by a filtration scheme to remove final aggregates and particulate matter.

Recovery can be performed by a variety of techniques including spray drying, rotary evaporation or precipitation, all of which serve to remove the fluorinated alcohol. Generally, the filtered solution is rotary evaporated to dryness at 37°–40° C. under high vacuum or precipitated from solution with a suitable solvent. Rotary evaporation is preferred. The resulting solid is dried under vacuum at 37°–40° C. to remove residual solvent. The polypeptide so recovered may then be used to manufacture liposomal pulmonary surfactant by ethanolic injection using techniques known in the art.

Suitable fluorinated alcohols for use in the present invention include 2,2,2-triflouroethanol; 1,1,1,3,3,3-hexafluoro-2 propanol and other fluorinated alcohols. As stated, it is believed that the fluorinated alcohol acts as a "helix stabilizing" medium. Helical polypeptides show less tendency to aggregate than other secondary structure polypeptides. This effect is believed to be the result of properties of the fluorinated alcohol rather than the intrinsic properties of the polypeptide chain.

In another aspect of the invention, it has been observed that liposomal KL4 pulmonary surfactant manufactured in accordance with the present invention exhibits reduced viscosity when compared with product formulated without treatment with fluorinated alcohol by the present invention. One of the problems encountered in the formulation and performance of liposomal $KL_4$ drug product is that the viscosity of the drug product can limit effective distribution in the lung, thereby reducing in vivo activity. The present invention therefore improves performance of $KL_4$ liposomal pulmonary surfactant by reducing viscosity of the final drug product.

In an alternate method of the present invention, the pulmonary surfactant polypeptide can be treated with the fluorinated alcohol in the method described above and the resulting solution can be admixed with the ethanol solvent and used directly in the ethanol injection liposome manufacturing process. The fluorinated alcohol is then removed with the ethanol in the liposome manufacturing process by dialysis or evaporation using techniques known in the art.

The present invention is further illustrated by the following example.

EXAMPLE 1

Preparation of Soluble KL4 Pulmonary Surfactant Polypeptide

To a 5.0 liter reaction flask equipped with stirrer, constant temperature bath, temperature thermocouple, and solid addition funnel, add 1.95 liters of trifluoroethanol. With moderate stirring at a temperature of 27° C., solid KL-4 acetate (80.0 g) is added in a portion wise manner. After the addition is completed, the funnel and walls of the flask are rinsed with 0.05 liters of trifluoroethanol. The flask is then secured to the atmosphere and the resulting opalescent solution is stirred at 27° C. for approximately 24 hours. Representative samples of the opalescent solution are taken at approximately t=0, t=5 h, t=7 h, and t=24.5 h time intervals. These samples are subjected to OD 450 um UV, FTIR, CD, clarity (Nessler tube), and viscosity (falling ball type) measurements for informational purposes.

Analysis of the FT-IR spectra (FIG. 1) indicates that the secondary structure in TFE has converted from β-Sheet to α-helix. Strong absorption bands at 1655 and 1548 cm$^{-1}$ are indicative of intra-molecular hydrogen bonding (α-helix). The conversion appears to be complete upon dissolution of the peptide in TFE ($t_0$=10 minutes after addition of $KL_4$) since there is no change in the amide I and II regions in the FT-IR spectra over the incubation period.

The OD450 analysis, as shown in Table 1, shows little aggregation at the $t_0$ point (10 minutes after addition of $KL_4$) with relatively low OD450 values that are less than 0.08. Through the course of incubation the OD450 values are constantly changing within the range of 0.01 to 0.03 after $t_0$. This could be the result of equilibration of the system and an oscillation between different aggregation states.

TABLE 1

OD450 and Minimum Mean Ellipicity values.

| Time (hrs) | OD 450 | Minimum ellipicity (wavelength) |
|---|---|---|
| 0 | 0.0725 | −23029.1 (207.4) |
| 2 | 0.0204 | −31540.9 (207.2 nm) |
| 5 | 0.0165 | −28013 (207.3) |
| 7 | 0.0234 | −31543.4 (207.6 nm) |
| 24.5 | 0.0124 | −35074.1 (207.2 nm) |
| 24.5 (filtered) | 0.0067 | −31808 (207.3 nm) |

Figure 2:
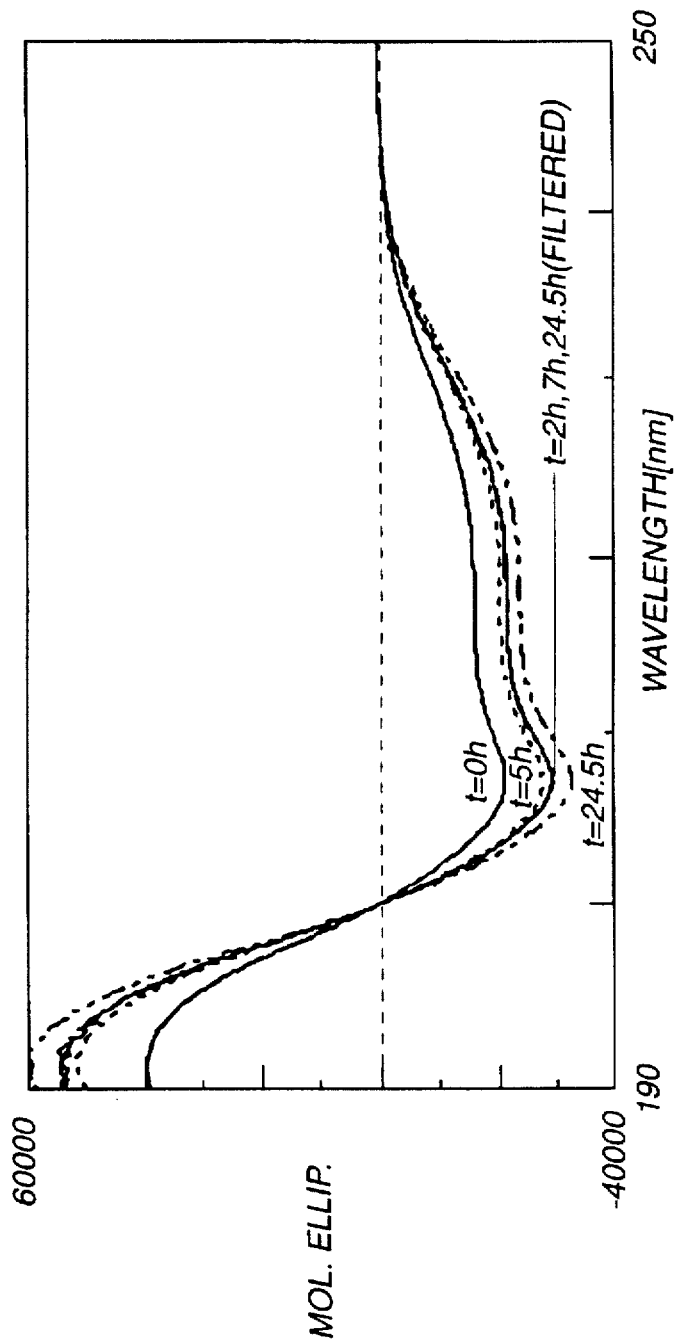
FIG. 2 shows the CD spectra of the polypeptide, $KL_4$-Acetate, in TFE during the incubation, treated in accordance with the present invention.

The CD spectra (FIG. 2) follows a similar pattern with minimum ellipicities reported between −25000 and −33000 [θ](deg.cm$^2$/dmole) and an isobestic point at 200 nm indicating that very little, in terms of secondary structure is different during the incubation period. The differences in the minimum mean molar ellipicities is likely due to different aggregation states of the peptide. The IR data suggests that the secondary structure of the peptide is not changing and is almost exclusively helical. CD and OD450 data suggests that the peptide is forming helical "bundles" of dimers, trimers, etc. and is changing constantly to some degree during the incubation in TFE.

After the 24.5 h incubation period, the resulting solution is then vacuum filtered over Whatman #1 filter paper. A sample of the filtrate is then removed for CD and OD450 assessment. The filtrate is then concentrated under vacuum (24–28 inches Hg) by rotary evaporation at 37°–38° C. to a solid residue.

The resulting solid is then passed through 60 mesh screen and dried further on the rotary evaporator under the same temperature and pressure conditions until TFE content of less than ten percent is present.

Under proper ventilation and dust protection guidelines, the product is transferred to a polypropylene container and stored at −20° C. A final mass yield of 82.64 g is obtained. An assay adjusted yield of 68.4 g (91.7%) of TFE treated KL-4 is obtained as a white to off white powder. $[\alpha]_D^{20}$ (c=0.1, 10% Hac), −40.79; MW=2470.2.

Figure 3A:
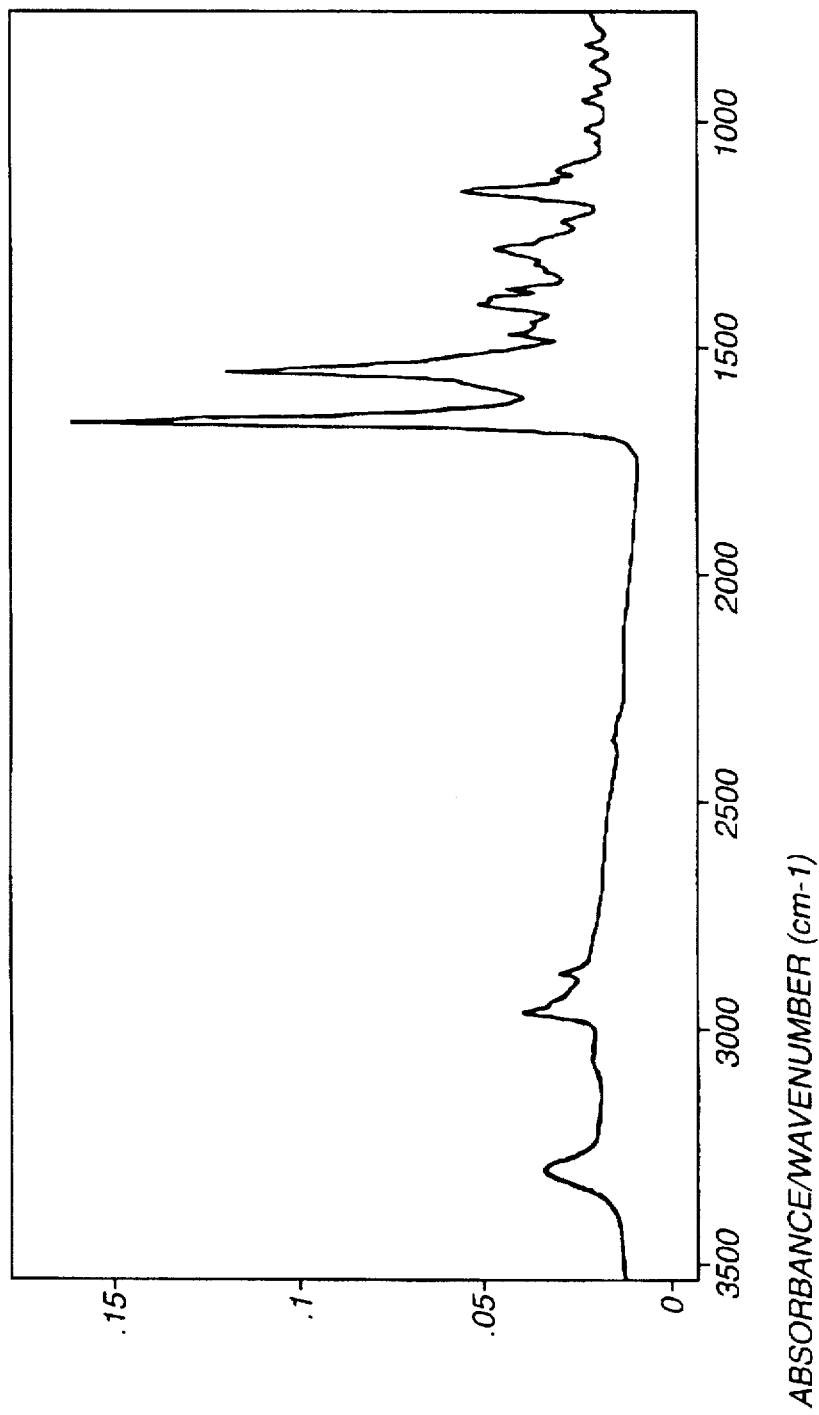
Figure 4B:
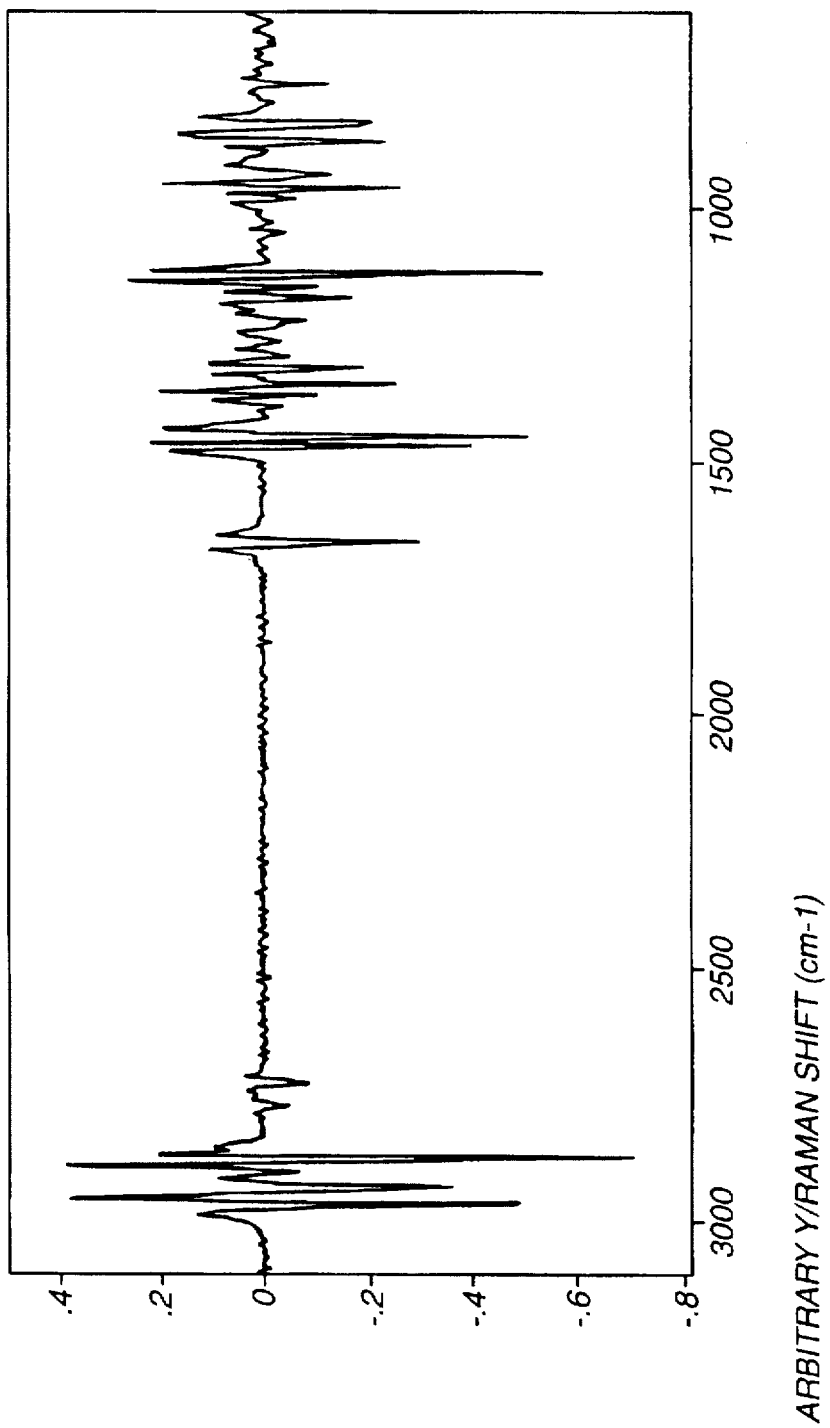

Analysis of the FT-IR spectra (FIGS. 3A and 3B) of the solid peptide treated in accordance with the present invention, indicate a large contribution of intra-molecular hydrogen bonding (α-helix) with strong absorption bands in the region of 1656–1657 cm$^{-1}$ (amide 1) and 1537–1548 cm$^{-1}$ (amide II). FT-Raman analysis of the samples in the solid state (FIGS. 4A and 4B) also indicate that the peptide is predominantly helical with a strong Amide I band at 1656 cm$^{-1}$ and an Amide III band at 1313 cm$^{-1}$.

Figure 5:
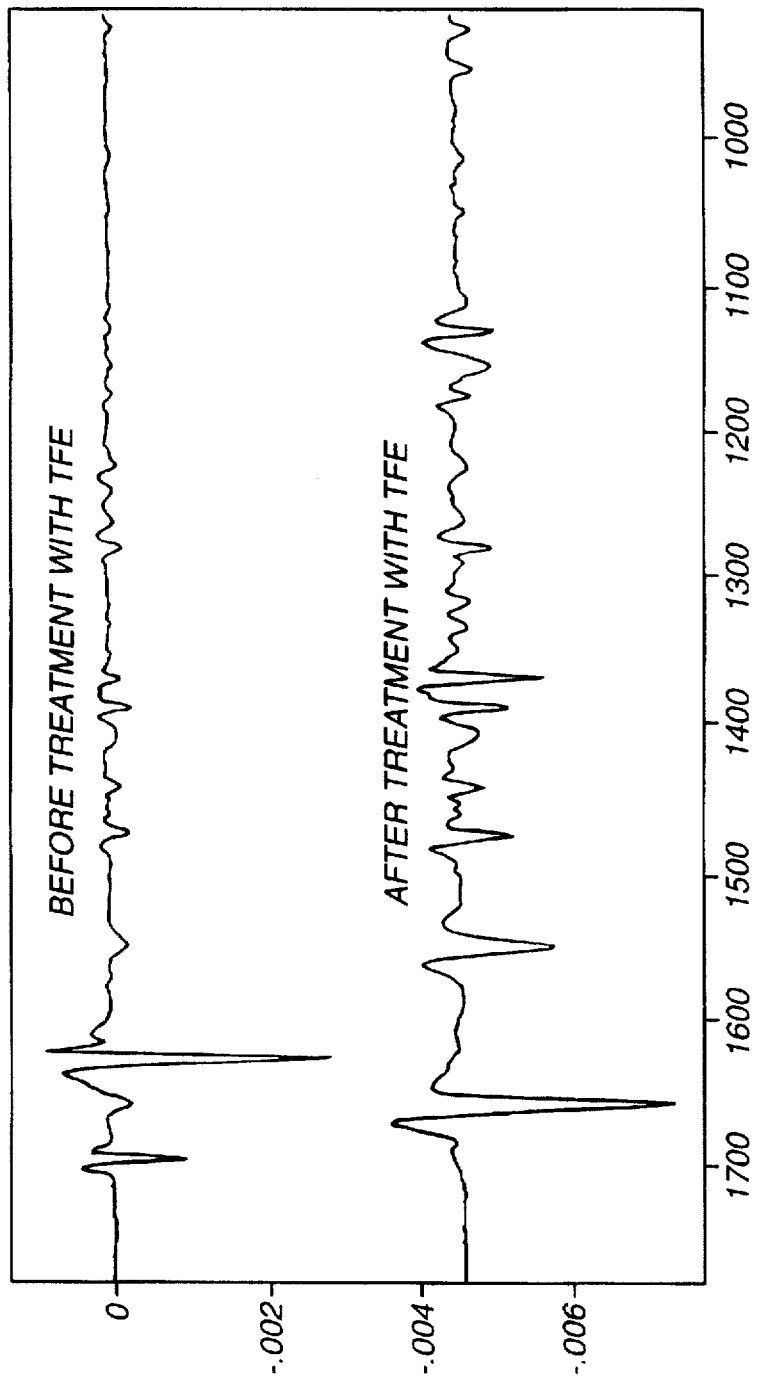
FIG. 5 shows the FT-IR analysis of polypeptide secondary structure of the solid $KL_4$-Acetate before and after treatment in accordance with the present invention. Second derivative spectra of Amide I, II, III regions.

FIG. 5 is an expansion of the FT -IR spectra (Amide I, II, II region indicative of secondary structure) of the polypeptide $KL_4$ before and after TFE treatment. The spectrum of the before treatment polypeptide has strong signals in the IR spectra at 1694 and 1628 cm$^{-1}$ which are indicative of intermolecular hydrogen bonding (β-Sheet). Weak absorption bands at 1658 cm$^{-1}$ and 1546 cm$^{-1}$ suggests the presence of some intramolecular hydrogen bonding (α-helix) in these samples. The spectrum of the solid polypeptide after treatment with TFE has strong absorption bands in the region of 1656–1657 cm$^{-1}$ (amide I) and 1537–1548 cm$^{-1}$ (amide II) indicating a large contribution of helical structure with very little evidence of β-Sheet structure present.

Figure 6:
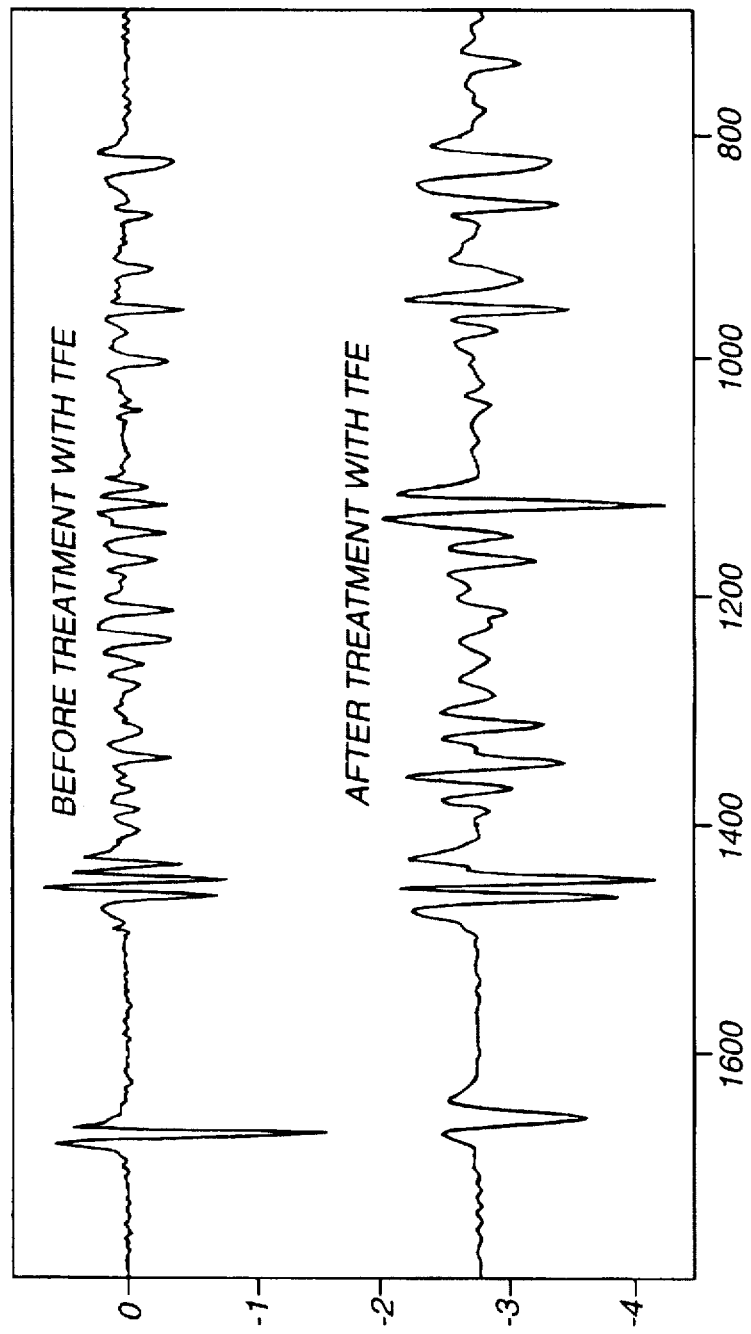
FIG. 6 shows the FT Raman analysis of polypeptide secondary structure of the solid $KL_4$-Acetate before and after treatment in accordance with the present invention. Second derivative spectra of Amide I, II, III regions.

FIG. 6 is an analysis of the amide I (1640–1680 cm$^{-1}$ and amide III (1220–1300 cm$^{-1}$) regions of the RAMAN spectrum. The spectrum of the polypeptide before treatment with TFE exhibits a strong signal at 1671 cm$^{-1}$ indicative of inter-molecular hydrogen bonding β-Sheet which is in agreement with the IR data. Signals at 1239 and 1213 cm$^{-1}$ (amide III) also suggest the presence of inter-molecular hydrogen bonding β-Sheet. The spectrum of the solid polypeptide after treatment with TFE indicates that the polypeptide is predominantly helical with a strong Amide I band at 1656 cm$^{-1}$ and an Amide III band at 1313 cm$^{-1}$.

Figure 7:
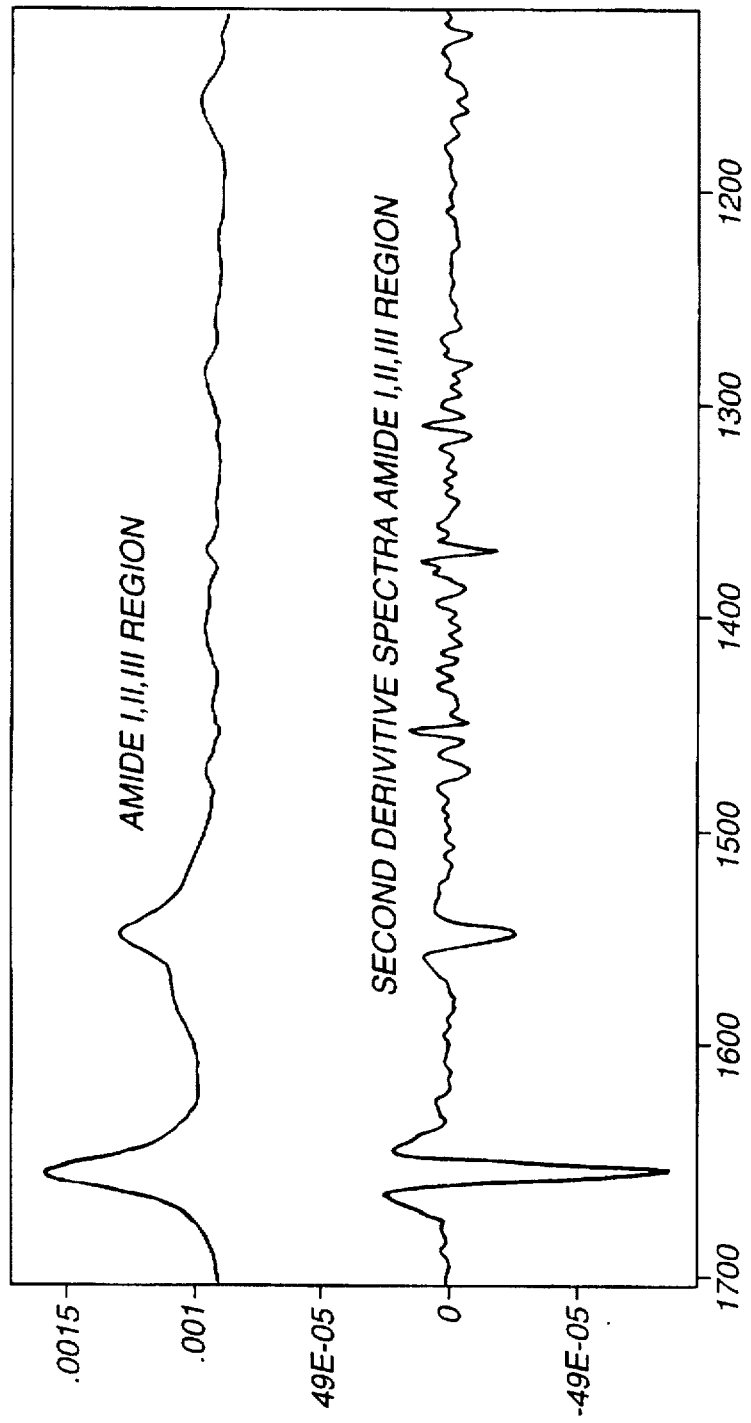
FIG. 7 shows the FT-IR spectrum of the solid polypeptide after treatment with TFE dissolved in 95% EtOH (5 mg/mL, 45° C.).
Figure 8:
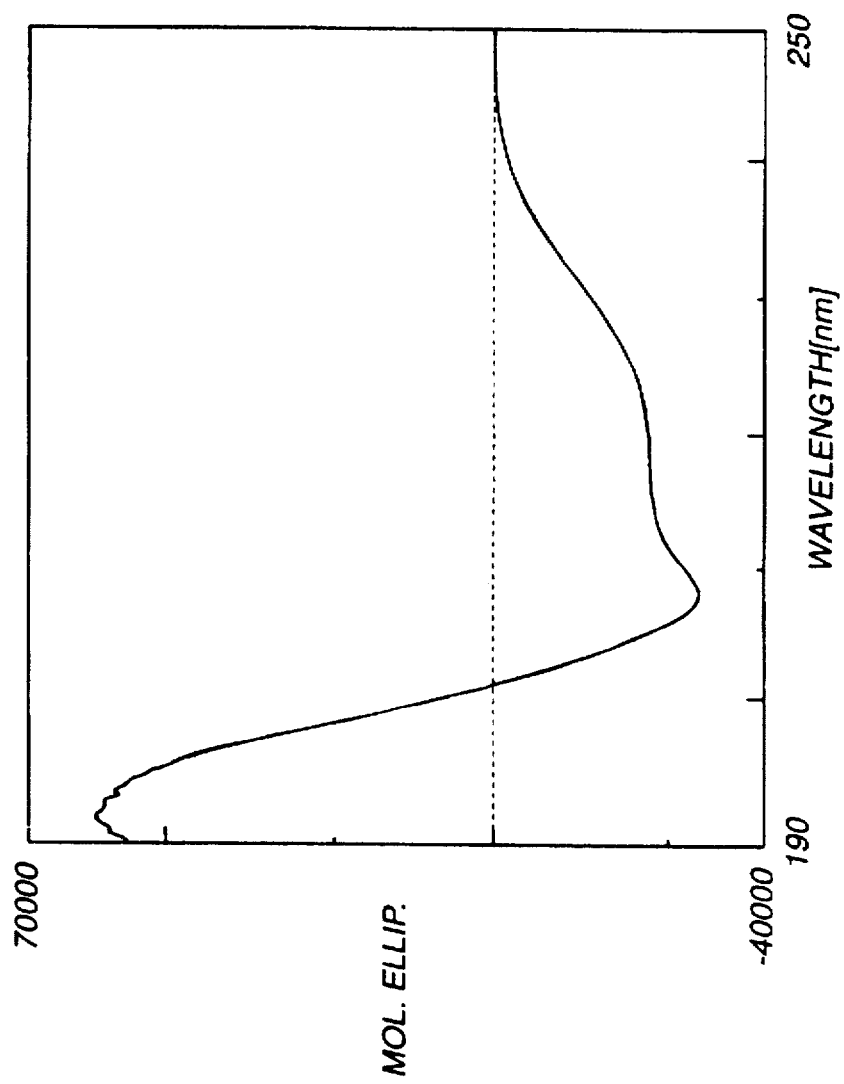
FIG. 8 shows the Circular Dichroism (CD) spectrum of the solid polypeptide after treatment with TFE dissolved in 95% EtOH (5 mg/mL 45° C.).

The sample was dissolved in 95% EtOH (5 mg/mL) to yield a clear non viscous solution. The solution was analyzed by IR and CD spectroscopy. Analysis of the FT-IR spectra (FIG. 7) indicate the peptide is predominantly helical in 95% EtOH with strong absorption bands in the region of 1656–1657 cm$^{-1}$ (amide I) and 1537–1548 cm$^{-1}$ (amide II) indicating a large contribution of helical structure with very little evidence of (β-Sheet) structure present. The analysis of the CD (FIG. 8) curve generated from this solution confirm the IR results. The solution was incubated at 45° C. for 40 minutes and the OD450 monitored over time. (TABLE 2). At time zero, the low OD450 value (<0.05) indicate that there is very little aggregation initially. Over time the OD450 value gradually increases indicating that the peptide is aggregating in solution (solution was still clear and non viscous).

TABLE 2

| OD450 values for peptide dissolved in 95% EtOH (5 mg/ml) | | | | | |
|---|---|---|---|---|---|
| | OD450 | | | | |
| Lot | t = 0 min | t = 10 min | t = 20 min | t = 30 min | t = 40 min |
| BO | 0.0199 | 0.0173 | 0.0131 | 0.0589 | 0.0681 |

Soluble KL$_4$ pulmonary surfactant polypeptide, prepared by the process described hereinabove, may be used to manufacture liposomal drug product in accordance with methods known in the art and hereinbefore described.

(a) preparing a solution of the polypeptide or salt or ester thereof in a fluorinated alcohol at a concentration of about 5 to 40 mg/ml;

(b) incubating for a period of time sufficient to achieve an optical density at 450 nanometers of less than 0.06;

(c) filtering; and (d) removing the fluorinated alcohol to recover solid, soluble polypeptide.

2. The process of claim 1 wherein the polypeptide is a linear polypeptide comprising at least 10 amino acid residues and no more than 60 amino acid residues, including a sequence having alternating hydrophobic and hydrophilic amino acid regions represented by the formula $(Z_aU_b)_cZ_d$ wherein:

Z is a hydrophilic amino acid residue independently selected from the group consisting of R and K;

U is a hydrophobic amino acid residue independently selected from the group consisting of V,I,L, C and F;

a has an average value of about 1 to about 5;

b has an average value of about 3 to about 20;

c is 1 to 10; and d is 1 to 3.

3. The process of claim 2 wherein the polypeptide has the amino acid sequence KLLLLKLLLLKLLLLKLLLLK.

4. The process of claim 1 wherein the fluorinated alcohol is 2,2,2-triflouroethanol.

5. In a process for preparing liposomal pulmonary surfactant composition, wherein the liposomal pulmonary surfactant composition is comprised of a polypeptide and a pharmaceutically acceptable phospholipid, and wherein the liposome is prepared by dissolving the polypeptide and phospholipid in ethanol and injecting the resulting solution into an aqueous phase optionally containing a buffer solution, the improvement which comprises pre-treating the

We claim:

1. An improvement in the process of preparing liposomal pulmonary surfactant composition by ethanolic injection, wherein the liposomal pulmonary surfactant composition is comprised of a polypeptide and a pharmaceutically acceptable phospholipid, the improvement comprising preparing a form of the polypeptide, or salt or ester thereof, which exhibits enhanced solubility in ethanol, comprising the steps of:

polypeptide by dissolving the polypeptide in a fluorinated alcohol at a concentration of 5–40 mg/ml before adding it to the ethanol solution.

6. The process of claim 5 wherein the polypeptide has the amino acid sequence KLLLLKLLLLKLLLLKLLLLK.

7. The process of claim 5 wherein the fluorinated alcohol is 2,2,2-triflouroethanol.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 21 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:1:

```
Lys  Leu  Leu  Leu  Leu  Lys  Leu  Leu  Leu  Leu  Lys  Leu  Leu  Leu  Leu  Lys
 1                    5                        10                       15

Leu  Leu  Leu  Leu  Lys
         20
```